(12) United States Patent
Nishida et al.

(10) Patent No.: US 7,705,187 B2
(45) Date of Patent: Apr. 27, 2010

(54) PRODUCTION METHOD OF TRIHYDROCARBYLBORANE

(75) Inventors: Tadao Nishida, Osaka (JP); Yoshihiko Kambara, Osaka (JP)

(73) Assignee: Nippon Aluminum Alkyls, Ltd., Tokyo (JP)

( * ) Notice: Subject to any disclaimer, the term of this patent is extended or adjusted under 35 U.S.C. 154(b) by 114 days.

(21) Appl. No.: 11/666,154

(22) PCT Filed: Jul. 6, 2006

(86) PCT No.: PCT/JP2006/313494
§ 371 (c)(1),
(2), (4) Date: Apr. 24, 2007

(87) PCT Pub. No.: WO2007/007638
PCT Pub. Date: Jan. 18, 2007

(65) Prior Publication Data
US 2008/0287712 A1 Nov. 20, 2008

(30) Foreign Application Priority Data
Jul. 7, 2005 (JP) .............................. 2005-198940

(51) Int. Cl.
*C07F 5/02* (2006.01)
(52) U.S. Cl. ........................................................ 568/7
(58) Field of Classification Search ................ None
See application file for complete search history.

(56) References Cited

U.S. PATENT DOCUMENTS

| | | | |
|---|---|---|---|
| 2,951,093 A | 8/1960 | Anderson | |
| 3,042,723 A | 7/1962 | Jenker | |
| 3,049,407 A | 8/1962 | Koster | |
| 4,952,714 A * | 8/1990 | Welborn, Jr. | ................ 556/179 |
| 5,414,180 A * | 5/1995 | Geerts et al. | ................ 585/525 |

FOREIGN PATENT DOCUMENTS

| | | |
|---|---|---|
| JP | S 41-6751 | 4/1941 |
| JP | 47-8621 | 5/1972 |
| JP | H 3-258786 A | 11/1991 |

OTHER PUBLICATIONS

Ashby, {New Syntheses of Trialkylboranes, J. Am. Chem. Soc., 1959, 81(18), pp. 4791-4795}.*
Ashby, "Organic and Biological Chemistry," Journal of the American Chemical Society, vol. 81, No. 18, pp. 4791-4795, Sep. 20, 1959.
Brown et al., "Organoboranes. 39. Convenient Procedures for the Preparation of Methylboronic Acid and Trimethylboroxin," Organometallics, vol. 4, No. 5, pp. 816-821, May 1985.

* cited by examiner

*Primary Examiner*—Porfirio Nazario Gonzalez
*Assistant Examiner*—Chukwuma O Nwaonicha
(74) *Attorney, Agent, or Firm*—Fitch, Even, Tabin & Flannery

(57) ABSTRACT

The present invention provides a method for industrial production of trihydrocarbylborane which method is excellent both in quality and in cost. The present invention is concerned with production of trihydrocarbylborane, comprising a reaction synthesizing the trihydrocarbylborane and aluminum oxide from trihydrocarbylboroxine and trihydrocarbylaluminum, characterized in that the reaction is allowed to proceed so that the trihydrocarbylaluminum is present at the end of the reaction in an amount of 0.5 moles or more per mole of the aluminum oxide produced in the reaction.

17 Claims, 1 Drawing Sheet

PRODUCTION METHOD OF TRIHYDROCARBYLBORANE

This is Application is a 371 (U.S. National Phase) of PCT International Application PCT/JP2006/313494, filed Jul. 6, 2006, which designated the U.S. and that International Application was not published under PCT Article 21(2) in English, claims the foreign priority filing date benefit of Japanese Application 2005-198940, filed Jul. 7, 2005, and incorporates by reference the complete disclosures of the aforesaid applications.

TECHNICAL FIELD

The present invention relates to a production method of trihydrocarbylborane useful as organic synthesis reagent such as an olefin polymerization catalyst, a reducing agent and an alkylating agent.

BACKGROUND ART

The production method of trihydrocarbylborane (hereinafter abbreviated as TRB) is described, for example, by taking as an example a production method of a trialkylborane.

A production method of TRB in which trialkoxyborane is reacted with trialkylaluminum is disclosed, for example, in Patent Document 1 (Japanese Patent Laid-Open No. 47-8621) and others.

$$B(OR)_3 + AlR_3 \rightarrow BR_3 + Al(OR)_3 \qquad (1)$$

R: alkyl

When this reaction is carried out in industrial production, it is necessary that the by-produced trialkoxyaluminum be hydrolyzed to be separated as aluminum hydroxide, and the alcohol be recovered and then reacted with boric acid to be again converted back into a trialkoxyborane; for that purpose, equipment is to be augmented and the number of the operation steps are also to be increased; the volume of the by-product exceeds that of TRB as the target product, and hence the volume efficiency of the reaction vessel is low; further, organic liquid waste is also discharged in a large amount to necessitate the disposal thereof; from the reasons described above, the above-mentioned method is not an advantageous method for industrial production.

Another production method of TRB in which boron trihalide is reacted with trialkylaluminum is also disclosed, for example, in Patent Document 1 and others.

$$BX_3 + AlR_3 \rightarrow BR_3 + AlX_3 \qquad (2)$$

X=F, Cl, Br, I

In this reaction, boron trihalide as a raw material is expensive and highly toxic, and hence an industrial production of TRB based on this reaction seems to be impossible.

Patent Document 2 (U.S. Pat. No. 2,951,093) discloses a method in which boron oxide is reacted with ethylaluminum sesquichloride, and Patent Document 3 (U.S. Pat. No. 3,042,723) discloses a method in which borax is reacted with ethylaluminum sesquichloride to produce TRB; however, according to the knowledge of the present inventors, any of these is low in reaction yield, and has been evaluated not to be applicable to industrial production.

Patent Document 4 (Japanese Patent Laid-Open No. 3-258786) describes a method for obtaining TRB by reacting trialkoxyboroxine with trialkylaluminum.

$$3R_3Al + (R-O-B-O-)_3 \rightarrow 3R_3B + (R-O-Al-O-)_3 \qquad (3)$$

This reaction suffers from the by-production of an alkoxy group-containing Al compound, similarly to the reaction of (1), causing a problem of the disposal thereof. Additionally, for production of trialkoxyboroxine, a method of Patent Document 5 (Japanese Patent Publication No. SHO 41-6751) is cited; in this method, the product is obtained as a solution containing an organic solvent such as carbon tetrachloride, thus a step for separating the organic solvent and other steps are required to make this method unsuitable for industrial production.

Well known is a production method of TRB in which trialkylborane is reacted with boron oxide to yield trialkylboroxine (hereinafter abbreviated as TRBO) (reaction (4)), and then TRBO is reacted with trialkylaluminum (hereinafter abbreviated as TRAL), and thus, TRB is newly produced in twice the amount used as the raw material (reaction (5)).

$$BR_3 + B_2O_3 \rightarrow R_3B_3O_3 \qquad (4)$$

$$R_3B_3O_3 + 2AlR_3 \rightarrow 3BR_3 + Al_2O_3 \qquad (5)$$

$$(4)+(5) BR_3 + B_2O_3 + 2AlR_3 \rightarrow 3BR_3 + Al_2O_3$$

For example, in Non-Patent Document 1 (ORGANIC AND BIOLOGICAL CHEMISTRY, September 20, 4791 (1959)), 0.2 mole of triethylboroxine (hereinafter abbreviated as TEBO) was added and reacted with 0.4 mole of triethylaluminum (hereinafter abbreviated as TEAL), then triethylborane (hereinafter abbreviated as TEB) was obtained with a yield of 95.6%. Non-Patent Document 1 also describes that aluminum oxide becomes white crystals having satisfactory fluidity in a flask.

Patent Document 6 (U.S. Pat. No. 3,049,407) describes that for the reaction between TRBO and TRAL, the TRBO to TRAL molar ratio is preferably 2, and a reaction method of adding TRAL into TRBO is preferable; and additionally, Patent Document 6 also recommends that a tertiary amine or TEB itself be used as the dispersion medium because aluminum oxide is handled in a liquid. Further, the concerned patent discloses a continuous distillation method in which a vertical thin-film evaporator is used in the distillation and the vapor of TRB is discharged from the top of the evaporator and the solid aluminum oxide is discharged from the bottom of the evaporator.

Patent Document 1: Japanese Patent Laid-Open No. 47-8621
Patent Document 2: U.S. Pat. No. 2,951,093
Patent Document 3: U.S. Pat. No. 3,042,723
Patent Document 4: Japanese Patent Laid-Open No. 3-258786
Patent Document 5: Japanese Patent Publication No. SHO41-6751
Patent Document 6: U.S. Pat. No. 3,049,407
Non-Patent Document 1: ORGANIC AND BIOLOGICAL CHEMISTRY, September 20, 4791 (1059).

DISCLOSURE OF THE INVENTION

Problems to be Solved by the Invention

Among the proposed production methods of TRB, the method in which the reaction (4) and the reaction (5) are combined seems to be a most excellent method to be industrially implemented because it is excellent in reaction yield, and the by-product is an inorganic material, namely, aluminum oxide, and organic waste is generated in a small amount. However, according to the knowledge of the present inventors, the reaction is carried out, as in the conventional techniques, by using TRAL in the vicinity of the theoretical amount of twice the moles of TRBO, gelation starts all over the synthesis liquid from around the end of the synthesis operation; the agitator trips and stops when the torque of the agitator is small, and subsequently the synthesis liquid is wholly solidified. Even when the torque is large and the agitation can thereby be continued, the agitation becomes difficult with the progress of the distillation operation of TRB, and eventually the gel sticks to the bottom of the distillation still, and the discharge operation of the gel becomes difficult.

It is to be noted that in the present description, the trihydrocarbylborane inclusive of trialkylborane is abbreviated as TRB and the trihydrocarbylaluminum inclusive of trialkylaluminum is abbreviated as TRAL, and the following description adopts these abbreviations.

As a countermeasure against the above-mentioned problem, as described in U.S. Pat. No. 3,049,407, a method in which aluminum oxide is fluidized by adding a tertiary amine or the like as a dispersion medium requires a step for separating the added tertiary amine, or causes the degradation of the product purity or other problems, and thus is disadvantageous for the industrial implementation. The use of TRB itself as the dispersion medium causes the loss of the targeted and expensive TRB, and results in the lack of economic rationality. Additionally, the present inventors have concluded that it is impossible to implement a continuous distillation operation in which TRB is recovered as a fraction of distillate while the solid aluminum oxide is being separated by introducing the mixed solution having no or such a remarkably low fluidity into the thin-film evaporator.

A method in which a paraffin oil is used as a dispersion medium may be possible, but, as shown in Comparative Example 2 of the present application, the gelation cannot be prevented and no satisfactory results have been obtained.

The present invention provides a new production method of TRB which method is free from the above described problems. Furthermore, the present invention provides a production method suitable for the industrial production excellent both in quality and in cost.

Means for Solving the Problems

The present inventors have made a diligent study for the purpose of solving the above described problems, and perfected the present invention by discovering that TRAL as a raw material serves as a satisfactory dispersion medium for aluminum oxide. Specifically, the production method of TRB of the present invention comprises a reaction synthesizing TRB and aluminum oxide from TRBO and TRAL, characterized in that the reaction is allowed to proceed so that TRAL is present at the end of the reaction in an amount of 0.5 moles or more per mole of the aluminum oxide produced in the reaction.

Additionally, the production method of TRB of the present invention comprises synthesis of TRB and aluminum oxide from TRBO and TRAL and subsequent separation of TRB by distillation, characterized in that the distillation is carried out in the presence of the TRAL in an amount of 0.5 moles or more per mole of the aluminum oxide.

ADVANTAGES OF THE INVENTION

The method of the present invention that is a rational production process of trihydrocarbylborane using no materials other than the raw materials enables the industrial production of trihydrocarbylborane excellent both in quality and in cost.

BRIEF DESCRIPTION OF THE DRAWING

In FIG. 1, the meanings of the reference numerals are as follows.

DESCRIPTION OF SYMBOLS

Figure 1:
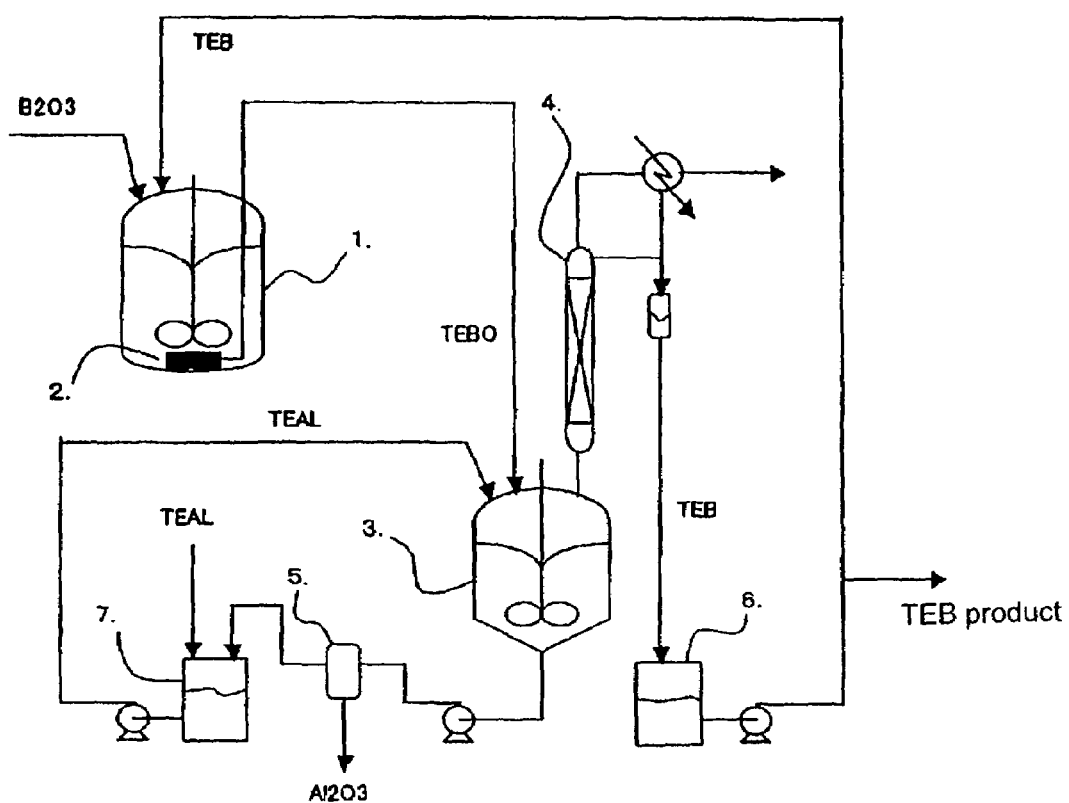
FIG. 1 is a view illustrating one of the embodiments of the production of TEB within the scope of the present invention.

1. TEBO synthesis reaction vessel
2. Filter
3. TEB reaction vessel doubling as distillation still
4. Fractionating tower
5. Filtering device
6. TEB receiver
7. TEAL receiver

BEST MODE FOR CARRYING OUT THE INVENTION

In the present invention, each of the hydrocarbyl groups in each of TRB and TRAL has 1 to 8 carbon atoms.

The hydrocarbyl group in the present invention has 1 to 8 carbon atoms, and is selected from an aliphatic hydrocarbon group, an alicyclic hydrocarbon group and an aromatic hydrocarbon group; specific examples of the hydrocarbyl group may include a methyl group, an ethyl group, a propyl group, a butyl group, a hexyl group, an octyl group, a cyclohexyl group, a phenyl group and a benzyl group. It is to be noted that different alkyl groups may be present in one and the same molecule in a mixed manner.

TRBO as the raw material is prepared by means of a method well known in the art. Boron oxide and TRB, for example, are placed in a pressure reaction vessel so as to be approximately equivalent in molar ratio to each other, and are allowed to react with each other at the reaction temperatures of 200 to 300° C. for 4 to 30 hours while being agitated in an inert gas atmosphere to prepare TRBO with a yield of 70 to 90%. The unreacted boron oxide is separated by filtration and the TRBO as the filtrate is transferred to a subsequent step for reaction with TRAL.

It is to be noted that it is rational from the viewpoint of process operation to dispose a filter, for filtration-separation of the unreacted boron oxide, inside a pressure reaction vessel for use in the synthesis of TRBO. Thus, the boron oxide separated and left in the reaction vessel can be used as it is in a subsequent reaction. The filtration property of the unreacted boron oxide is satisfactory, and various filters can be used; a metal mesh filter, for example, can be preferably used.

The TRBO synthesis reaction solution obtained as a filtrate is reacted with TRAL in a TRB synthesis reaction vessel in the next step to prepare TRB and aluminum oxide. In this stage of the method of the present invention, it is essential that TRAL be present at the end of the reaction in an amount of 0.5 moles or more per mole of the aluminum oxide produced with the progress of the reaction. Herewith, the phenomenon in which the aluminum oxide in the reaction solution is gelated and further, the whole reaction solution is solidified can be suppressed owing to the fact that the concomitantly present TRAL serves as a stable dispersion medium; the reaction solution is neither gelated nor solidified both through the reaction and through the next step for distilling TRB, and accordingly can maintain an easily handleable slurry state.

No particular constraint is imposed on the reaction that fulfills the above-mentioned conditions, but an example thereof is a procedure as follows: TRAL is beforehand placed in the reaction vessel in a total necessary amount, namely, in an amount 2.5 or more times, preferably, 3 to 6 times the moles of TRBO; and a TRBO synthesis reaction solution is dropped bit by bit over a period of 1 to 5 hours into the reaction vessel to react with TRAL under agitation and cooling. This procedure yields TRB with a yield of 95% or more. The reaction temperature varies depending on the hydrocarbyl groups contained in the raw materials, and is preferably set to fall within a range from room temperature to approximately 150° C. Another example of the reaction operation concerned is a method in which while the amount of TRAL is being maintained to be 2.5 or more times the moles of TRBO, both raw materials are simultaneously fed into the reaction vessel to react with each other, this method also giving a satisfactory result. It is to be noted that this method of simultaneous feeding of the raw materials has been found to lead to a tendency that the aluminum oxide produced in the reaction has a larger grain size of the obtained crystal thereof.

Also, even in the reaction to be carried out by adding TRAL to TRBO, when the molar ratio TRAL/TRBO is approximately 1.1 or less, preferably 1.0 or less, no precipitation of gelated aluminum oxide occurs; hence, the TRAL and the TRBO that have been preliminarily reacted with each other in the above-mentioned molar ratio range may be added to TRAL, and the reaction may be allowed to proceed in such a way that the amount of TRAL is 2.5 times the moles of TRBO at the end of the reaction.

From the reaction solution thus obtained, TRB as a product is recovered by distillation; in the method of the present invention, the distillation is carried out by making TRAL present in an amount of 0.5 moles or more per mole of the aluminum oxide in the reaction solution. When the amount of TRAL is small, the fluidity of the still bottom solution becomes poor, and when the amount of TRAL is large, the boiling point of the reaction solution is raised and the recovery rate of TRB is decreased. Therefore, the amount of TRAL is preferably approximately 0.5 or more times and 6 or less times the moles of the aluminum oxide. In particular, the amount of TRAL of approximately 1 or more times and 3 or less times the moles of the aluminum oxide is excellent from the viewpoints of the handlability of the reaction solution and the distillation recovery rate of TRB. Thus, from the still bottom solution maintaining a satisfactory fluidity, aluminum oxide can be easily removed by filtration, and TRAL as the filtrate can be again used in the reaction (5) with TRBO.

In an alternative method for obtaining TRB of the present invention, first, aluminum oxide is removed by filtration from the reaction product, thereafter the filtrate is separated and distilled to recover TRB as a product, and the still bottom solution containing TRAL as the main component can be again used in the reaction (5) with TRBO. In this case, the distillation step does not involve any solid matter, and hence any trouble due to the concentration of aluminum oxide in the distillation still is not caused, so that the distillation can be stably carried out.

If expensive TRBO and TRB remain by adhesion to the aluminum oxide cake at the time of the filtration of aluminum oxide, it will result in a loss from the viewpoint of the process economics; thus, also preferable is a method in which the aluminum oxide cake is washed with relatively inexpensive TRAL and the washing waste is also used as a raw material.

Additionally, if needed, the reaction product may be diluted with TRAL in a process for working up thereof to work it up better.

A preferable distillation method is such that the reaction vessel, as it is, is used as a distillation still and a fractionating tower is disposed thereabove the still is heated under agitation; either a plate tower or a packed tower can be used as the fractionating tower, the packed tower being preferable because it can be small in size. In the case of TEB, for example, the boiling points of TEB and TRAL are 96° C. and 194° C. to be largely different from each other, and thus, a sufficient separation efficiency and a sufficient distillation yield can be obtained by operating under the conditions that the number of the separation stages is 3 to 10, the reflux ratio is 1 to 10, the pressure ranges from atmospheric pressure down to a reduced pressure of 30 kPa, and the temperature ranges approximately from 95 down to 65° C.

The still bottom solution after distillation is a TRAL slurry solution of aluminum oxide. The slurry solution is taken out of the still, made to pass through a filtering device to separate aluminum oxide therefrom, and TRAL as the filtrate thus obtained is again used in the reaction (5). As for the aluminum oxide crystal obtained at this stage, the crystal obtained by the method of simultaneous feeding of the raw materials is larger in grain size, as described above, and hence the filtration property thereof tends to be satisfactory. The filter of the filtering device may be made of a ceramic, a cloth, a metal or the like. The TRAL as the filtrate has undergone the reaction and the distillation, so that there has been a fear of the compositional change and the quality degradation thereof, but has been able to be used again in the reaction (5) without causing any problem in such a way that the reaction achievement and the quality of the TRB thus obtained have not exhibited any changes.

In another embodiment, first the reaction solution is passed through the filtering device to separate aluminum oxide, the filtrate is distilled to recover the product TRB, and the still bottom solution containing TRAL as the main component thereof is used in the reaction (5). The distillation conditions, the filtering device and the like are the same as described above. The thus obtained still bottom solution can be used again in the reaction (5), and the reaction achievement and the quality of the TRB thus obtained have not exhibited any changes.

EXAMPLES

Example-1

In a 1-L four-neck flask equipped with an agitator, 3 moles of triethylaluminum was placed, and 1 mole of triethylboroxine contained in a dropping funnel was dropped into the flask over a period of 3 hours to react with triethylaluminum. In this case, the reaction solution was cooled with a cooling medium so as for the temperature of the reaction solution to be maintained at 70° C. Then, the flask was raised in temperature to 100° C. in an oil bath, and 2.9 moles of triethylborane at 95° C. was obtained from the top of a tower packed with Dixon packing. An aluminum oxide-containing slurry solution was left in the flask. The slurry solution was filtered with a glass filter (25G-4; pore size: 5 to 10 μm) under a reduced pressure (150 Torr) over a period of 30 minutes. On the filter, 0.98 mole of a white powder of aluminum oxide was left, and the colorless, transparent filtrate was 1.04 moles of triethylaluminum. The yield of triethylborane was 97.1%. The purity of the obtained triethylborane was 99.9% or more on the basis of the results of the NMR analysis and the metal analysis carried out after hydrolysis.

Example-2

In a 1-L four-neck flask equipped with an agitator, from a dropping funnel containing 3 moles of triethylaluminum and from another dropping funnel containing 1 mole of triethylboroxine, the respective contents in these dropping funnels were simultaneously dropped over a period of 3 hours each at a rate maintained approximately constant, and thus the simultaneous-addition reaction was completed. In this case, the reaction solution was cooled with a cooling medium so as for the temperature of the reaction solution to be maintained at 70° C. Then, the flask was raised in temperature in an oil bath, and 2.85 moles of triethylborane at 95° C. was obtained from the top of a tower packed with Dixon packing. A white aluminum oxide-containing slurry solution was left in the flask. The slurry solution was filtered with a glass filter (25G-3; pore size: 20 to 30 μm) under a reduced pressure (150 Torr) over a period of 10 minutes. On the filter, 0.95 mole of aluminum oxide was left, and the colorless, transparent filtrate was 1.08 moles of triethylaluminum. The yield and the purity of triethylborane were 95.0% and 99.9% or more, respectively.

Example-3

In a 1-L four-neck flask equipped with an agitator, 4 moles of triethylaluminum was placed, and 1 mole of triethylboroxine contained in a dropping funnel was dropped into the flask over a period of 3 hours to react with triethylaluminum. In this case, the reaction solution was cooled with a cooling medium so as for the temperature of the reaction solution to be maintained at 70° C. Then, the flask was raised in temperature to 100° C. in an oil bath, and 2.93 moles of triethylborane at 95° C. was obtained from the top of a tower packed with Dixon packing. An aluminum oxide-containing slurry solution was left in the flask. The amounts of the aluminum oxide and the triethylaluminum contained in the slurry solution were 0.98 mole and 2.04 moles, respectively. The yield and the purity of triethylborane were 97.6% and 99% or more, respectively.

Example-4

In a 1-L four-neck flask equipped with an agitator, 4 moles of tributylaluminum was placed, and 1 mole of tributylboroxine contained in a dropping funnel was dropped into the flask over a period of 2 hours to react with tributylaluminum. In this case, the reaction solution was cooled with a cooling medium so as for the temperature of the reaction solution to be maintained at 100° C. Then, the flask was raised in temperature to 140° C. in an oil bath, the reaction solution was aged for 3 hours, and thereafter 2.9 moles of tributylborane at 80° C. was obtained from the top of a tower packed with Dixon packing under a reduced pressure distillation condition of 6.5 mmHg. An aluminum oxide-containing slurry solution was left in the flask. The amounts of the aluminum oxide and the tributylaluminum contained in the slurry solution were 0.96 mole and 2.07 moles, respectively. The yield and the purity of tributylborane were 96.7% and 98% or more, respectively.

Example-5

In a 1-L four-neck flask equipped with an agitator, 4 moles of tripropylaluminum was placed, and 1 mole of tripropylboroxine contained in a dropping funnel was dropped into the flask over a period of 2 hours to react with tripropylaluminum. In this case, the reaction solution was cooled with a cooling medium so as for the temperature of the reaction solution to be maintained at 100° C. Then, the flask was raised in temperature to 140° C. in an oil bath, the reaction solution was aged for 3 hours, and thereafter 2.9 moles of tripropylborane at 75° C. was obtained from the top of a tower packed with Dixon packing under a reduced pressure distillation condition of 36 mmHg. An aluminum oxide-containing slurry solution was left in the flask. The amounts of the aluminum oxide and the tripropylaluminum contained in the slurry solution were 0.96 mole and 2.07 moles, respectively. The yield and the purity of tripropylborane were 97.1% and 98.5% or more, respectively.

Comparative Example-1

In a 1-L four-neck flask equipped with an agitator, 2 moles of triethylaluminum was placed. From the time by which 0.80 mole of triethylboroxine had been dropped to react with triethylaluminum into the flask from a dropping funnel containing 1 mole of triethylboroxine, the viscosity of the synthesis solution was increased, and at the time by which 0.85 mole of triethylboroxine had been dropped, the state of the flask content became a solidified state and the agitator was stopped. At this time, the temperature of the reaction solution was maintained at 70° C. After the rest of triethylboroxine had been added, the flask was raised in temperature from 120° C. to 140° C. in an oil bath, and 1.34 moles of triethylborane at 95° C. was obtained from the top of a tower packed with Dixon packing. A white solid matter and a highly viscous matter were left in the flask. The yield of triethylborane was 44.7%.

Comparative Example-2

In a 1-L four-neck flask equipped with an agitator, 1 mole of triethylaluminum and 120 g of liquid paraffin were placed. At the time by which 0.43 mole of triethylboroxine had been dropped to react with triethylaluminum into the flask from a dropping funnel containing 0.5 mole of triethylboroxine, the synthesis solution was converted from a gel state to a solidified state. Further addition of 120 g of liquid paraffin into the reaction flask failed in elimination of the solidified state, which was not changed. At this time, the temperature of the reaction solution was maintained at 70° C. After the rest, namely, 0.1 mole of triethylboroxine had been added, the flask was raised in temperature from 120° C. to 140° C. under atmospheric pressure, and 0.95 mole of triethylborane at 95° C. was obtained from the top of a tower packed with Dixon packing. The liquid paraffin layer and a white solid matter adhered to the bottom of the flask were left in the flask. The yield of triethylborane was 63.3%.

Comparative Example-3

In a 1-L four-neck flask equipped with an agitator, 0.63 mole of triethylboroxine was placed. At the time by which 0.7 mole of triethylaluminum had been dropped into the flask from a dropping funnel containing 1.26 moles of triethylaluminum, the synthesis solution started to become clouded, and at the time by which 0.73 mole of triethylaluminum had been dropped, the synthesis solution was gelated to become a solidified state. Because the continuation of the agitation became impossible, 200 ml of liquid paraffin was added to the flask, and the rest, namely, 0.53 mole of triethylaluminum was drooped into the flask to react with triethylboroxine. The state of the content of the flask after the reaction was such that a gelated and solidified matter remained adhered to the inner wall of the flask without forming a dispersed state. The flask was heated up to 180° C. to carry out distillation, and consequently, the yield of triethylborane was 71%.

Comparative Example 4

In a 1-L four-neck flask equipped with an agitator, 0.5 mole of tributylboroxine was placed. At the time by which 0.6 mole of tributylaluminum had been dropped into the flask from a dropping funnel containing 1 mole of tributylaluminum, the synthesis solution was gelated to become a solidified state. Because the continuation of the agitation became impossible, 200 ml of liquid paraffin was added to the flask, and the rest, namely, 0.4 mole of tributylaluminum was dropped into the flask to react with triethylboroxine. In this case, the reaction solution was heated with a heating medium so as for the temperature of the reaction solution to be maintained at 100° C. Then, the flask was raised in temperature to 140° C., the reaction solution was aged for 3 hours, and thereafter 0.95 mole of tributylborane at 80° C. was obtained from the top of a tower packed with Dixon packing under a reduced pressure distillation condition of 6.5 mmHg. A gelated solid matter and a highly viscous matter were left in the flask. The yield of tributylborane was 63.3%.

Example-6

The slurry-like residual mixture in the flask in Example-2 was filtered with a 10-μm filtering device to recover 1.8 moles of triethylaluminum. This filtering was able to be carried out smoothly. In a 1-L four-neck flask equipped with an agitator, 1.8 moles of the recovered triethylaluminum and additional 2.2 moles of triethylaluminum were placed in combination, and 1 mole of triethylboroxine contained in a dropping funnel was dropped into the flask over a period of 3 hours to react with triethylaluminum. In this case, the reaction solution was cooled with a cooling medium so as for the temperature of the reaction solution to be maintained at 70° C. Then, the flask was raised in temperature to 100° C. in an oil bath, and 2.92 moles of triethylborane at 95° C. was obtained from the top of a tower packed with Dixon packing. An aluminum oxide-containing slurry solution was left in the flask. The amounts of the aluminum oxide and the triethylaluminum contained in the slurry solution were 0.98 mole and 2.04 moles, respectively. The yield of triethylborane was 97.3%. The purity of the obtained triethylborane was 99% or more on the basis of the results of the NMR analysis and the metal analysis carried out after hydrolysis.

Example-7

With reference to FIG. 1, the TEB production flow is described as a representative example. A TEBO synthesis reaction vessel denoted by reference numeral 1 is a 100-L stainless steel vessel which has a metal mesh filter 2 disposed thereinside, and agitating and cooling means. A TEB synthesis reaction vessel, denoted by reference numeral 3, doubling as a distillation still is a 250-L stainless steel vessel which has an agitating means, and a heating/cooling means. To the reaction vessel 3 connected is a distillation tower 4 in which 16-mm Raschig rings of 100 mm in inside diameter are packed along a height of 2 m. Reference numeral 5 denotes a filtering device having a 10-μm metal mesh filter disposed thereinside.

In the vessel 1, 25.6 kg (0.368 kmol) of boron oxide and 36.1 kg (0.368 kmol) of TEB were placed, and were reacted with each other in a nitrogen atmosphere at a reaction temperature of 210° C. under a pressure of 1.7 MPa for 24 hours. In the vessel 3, 154 kg (1.5 kmol) of TEAL was placed, and 55.5 kg filtrate TEBO and 2.32 Kg of TEB obtained by separating the unreacted boron oxide through the filter 2 were fed into the vessel 3 over a period of 4 hours while the solution temperature was being maintained at 70° C. Then, the solution temperature was raised to start the distillation operation. When the temperature exceeded 100° C., the distillation of TEB started. Thereafter, by regulating the reflux ratio to be 5 to 10, 99.5 kg (1.02 kmol) of TEB as the distillate was obtained in a receiver 6. In the vessel 1, 2.56 kg (0.037 kmol) of the unreacted boron oxide filtration-separated from the still bottom solution and additional 23.1 kg (0.33 kmol) of boron oxide were placed in combination, and then 35.9 kg (0.366 kmol) of the obtained TEB was also place, and the same reaction as described above was carried out to yield 55.5 kg of TEB. After distillation, the still bottom solution in the vessel 3 was composed of 33.7 kg (0.33 kmol) of aluminum oxide, 78.6 kg (0.688 kmol) of TEAL, 1.01 kg (0.01 kmol) of TEB and 1.13 kg (0.007 kmol) of TEBO; and the aluminum oxide was filtered through the filtering device 5. The filtrate was again fed into the vessel 3, and TEAL was further added so as for the total amount of TEAL to be 154 kg (1.5 kmol). Then, the solution obtained through the filter 2 was also fed into the vessel 3, and the TEB synthesis reaction was carried out and the distillation was also carried out in the same manner. This cycle was repeated 5 times. A stable, high quality product of TEB was obtained in an amount of 63 to 64 kg, and the yield thereof based on the consumed raw material TEAL was maintained at approximately 96%.

The invention claimed is:

1. A method for producing trihydrocarbylborane, comprising reacting trihydrocarbylboroxine and trihydrocarbylaluminum without another component as a solvent to obtain said trihydrocarbylborane and aluminum oxide, allowing the reaction to proceed so that the trihydrocarbylaluminum is present at the end of the reaction in an amount of 0.5 moles or more per mole of the aluminum oxide produced in the reaction, and recovering the trihydrocarbylborane by distillation.

2. The method according to claim 1, wherein the distillation is carried out in the presence of the trihydrocarbylaluminum in an amount of 0.5 moles or more per mole of the aluminum oxide.

3. The method according to claim 1, wherein the trihydrocarbylborane and the trihydrocarbylaluminum have a hydrocarbyl group of 1 to 8 carbon atoms.

4. The method according to claim 1, wherein the trihydrocarbylborane is triethylborane and the trihydrocarbylaluminum is triethylaluminum.

5. The method according to claim 2, wherein the trihydrocarbylborane and the trihydrocarbylaluminum have a hydrocarbyl group of 1 to 8 carbon atoms.

6. The method according to claim 2, wherein the trihydrocarbylborane is triethylborane and the trihydrocarbylaluminum is triethylaluminum.

7. The method according to claim 1, wherein the trihydrocarbylborane recovered has a purity of 98% or more.

8. The method according to claim 2, wherein the trihydrocarbylborane recovered has a purity of 98% or more.

9. A method for producing trihydrocarbylborane, comprising reacting trihydrocarbylboroxine and trihydrocarbylaluminum in a mixture consisting of the trihydrocarbylboroxine and the trihydrocarbylaluminum to obtain said trihydrocarbylborane and aluminum oxide, allowing the reaction to proceed so that the trihydrocarbylaluminum is present at the end of the reaction in an amount of 0.5 moles or more per mole of the aluminum oxide produced in the reaction, and recovering the trihydrocarbylborane by distillation.

10. The method according to claim 9, wherein the distillation is carried out in the presence of the trihydrocarbylaluminum in an amount of 0.5 moles or more per mole of the aluminum oxide.

11. The method according to claim 9, wherein the trihydrocarbylborane and the trihydrocarbylaluminum have a hydrocarbyl group of 1 to 8 carbon atoms.

12. The method according to claim 9, wherein the trihydrocarbylborane is triethylborane and the trihydrocarbylaluminum is triethylaluminum.

13. The method according to claim 9, wherein the trihydrocarbylborane recovered has a purity of 98% or more.

14. The method according to claim 10, wherein the trihydrocarbylborane and the trihydrocarbylaluminum has a hydrocarbyl group of 1 to 8 carbon atoms.

15. The method according to claim 10, wherein the trihydrocarbylborane is triethylborane and the trihydrocarbylaluminum is triethialuminum.

16. The method according to claim 10, wherein the trihydrocarbylborane recovered has a purity of 98% or more.

17. A method for producing trihydrocarbylborane comprising (a) reacting a solvent-free mixture of trihydrocarbylboroxine and trihydrocarbylaluminum to obtain a reaction mixture containing said trihydrocarbylborane and aiuminum oxide whereby trihydrocarbylaiuminum is present in said reaction mixture in an amount of 0.5 moles or more per mole of the aluminum oxide produced in the reaction, and then (b) recovering said trihydrocarbylborane from said reaction mixture by distillation.

* * * * *